US010383756B2

(12) United States Patent
Arnholt et al.

(10) Patent No.: US 10,383,756 B2
(45) Date of Patent: Aug. 20, 2019

(54) INTRAGASTRIC BALLOON DELIVERY SYSTEMS AND METHODS

(71) Applicant: Boston Scientific Scimed, Inc., Maple Grove, MN (US)

(72) Inventors: Devon N. Arnholt, Shoreview, MN (US); Joel T. Eggert, Plymouth, MN (US); James P. Rohl, Prescott, WI (US); Douglas D. Pagoria, Forest Lake, MN (US); Todd College, Little Canada, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 838 days.

(21) Appl. No.: 14/657,265

(22) Filed: Mar. 13, 2015

(65) Prior Publication Data

US 2015/0257912 A1    Sep. 17, 2015

Related U.S. Application Data

(60) Provisional application No. 61/953,030, filed on Mar. 14, 2014.

(51) Int. Cl.
*A61F 5/00* (2006.01)

(52) U.S. Cl.
CPC ............ *A61F 5/0089* (2013.01); *A61F 5/003* (2013.01); *A61F 5/0036* (2013.01)

(58) Field of Classification Search
CPC ...... A61F 5/003; A61F 5/0089; A61F 5/0036; A61M 2025/1054
See application file for complete search history.

(56) References Cited

U.S. PATENT DOCUMENTS

| | | | | |
|---|---|---|---|---|
| 5,964,730 A | * | 10/1999 | Williams | A61M 25/10 604/103 |
| 7,066,945 B2 | | 6/2006 | Hashiba et al. | |
| 8,142,514 B2 | * | 3/2012 | Geitz | A61F 5/0036 623/23.65 |
| 9,924,948 B2 | * | 3/2018 | Burnett | A61B 5/14539 |
| 2006/0161197 A1 | * | 7/2006 | Paul | A61L 29/005 606/195 |
| 2007/0198047 A1 | * | 8/2007 | Schon | A61B 17/320725 606/192 |
| 2007/0198048 A1 | * | 8/2007 | Behan | A61F 2/04 606/194 |
| 2007/0239284 A1 | * | 10/2007 | Skerven | A61F 5/0003 623/23.65 |

(Continued)

*Primary Examiner* — Matthew F DeSanto
(74) *Attorney, Agent, or Firm* — Bookoff McAndrews, PLLC

(57) ABSTRACT

According to aspects of the present disclosure, a system may include a loading device including an exterior surface. The system may also include an expandable member mounted on the exterior surface of the loading device. The expandable member may be configured to selectively transition between a collapsed state and an expanded state. The system may also include a covering mounted on the expandable member. The covering may extend around the expandable member and the loading device. The loading device may be configured to position the expandable member and the covering for mounting on an exterior surface of an elongate introduction sheath.

17 Claims, 5 Drawing Sheets

(56) References Cited

U.S. PATENT DOCUMENTS

| | | | |
|---|---|---|---|
| 2008/0228126 A1* | 9/2008 | Bessler | A61F 2/04 604/9 |
| 2012/0123525 A1* | 5/2012 | Kramer-Brown | A61L 31/022 623/1.34 |
| 2013/0035711 A1 | 2/2013 | Schwab et al. | |
| 2014/0039536 A1* | 2/2014 | Cully | A61B 17/0057 606/194 |

* cited by examiner

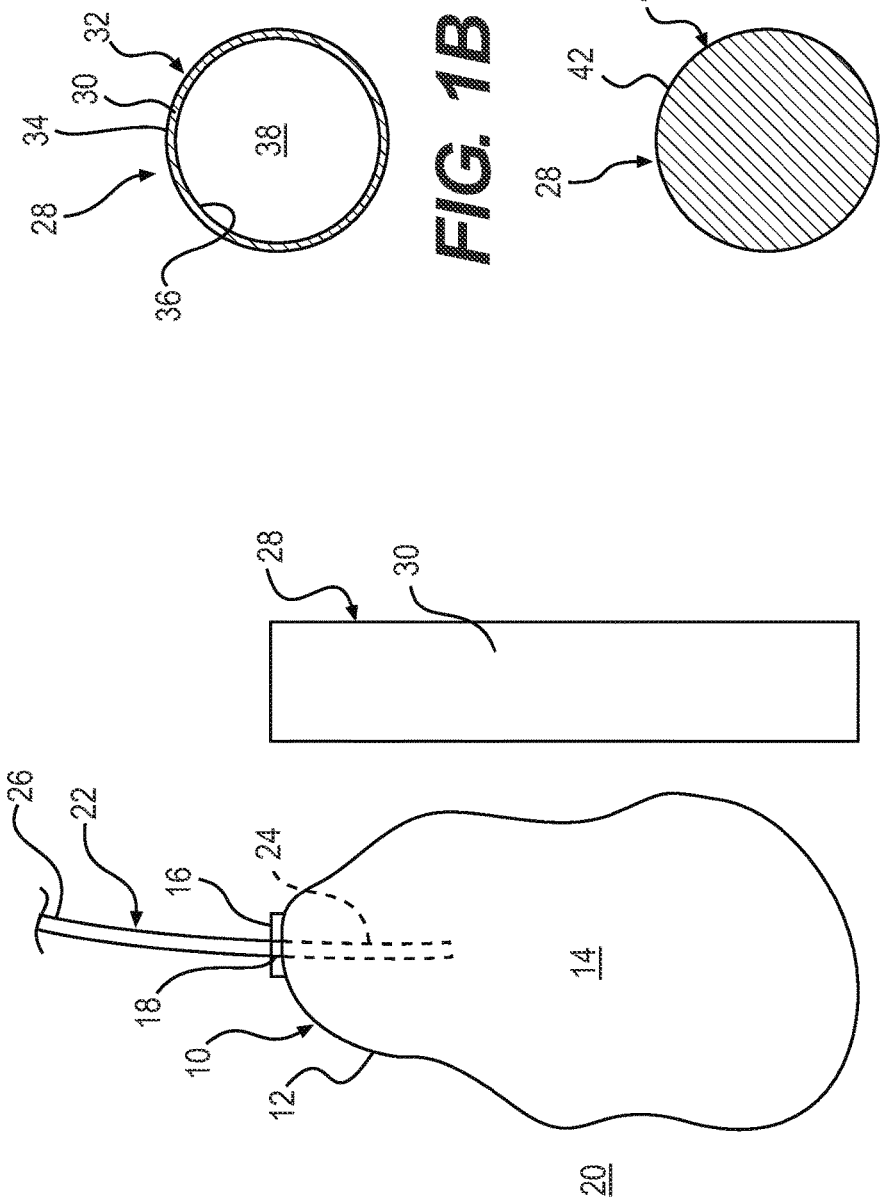

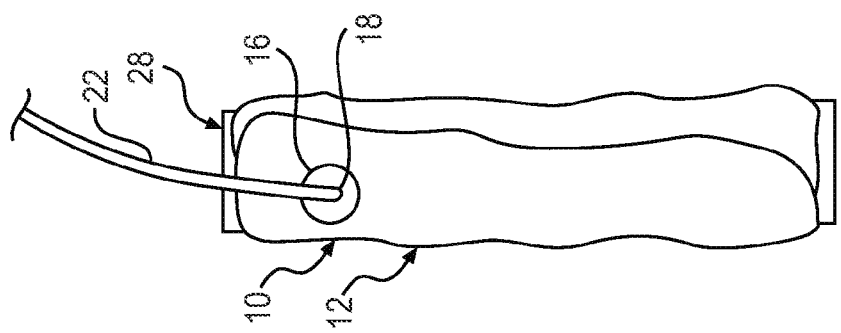
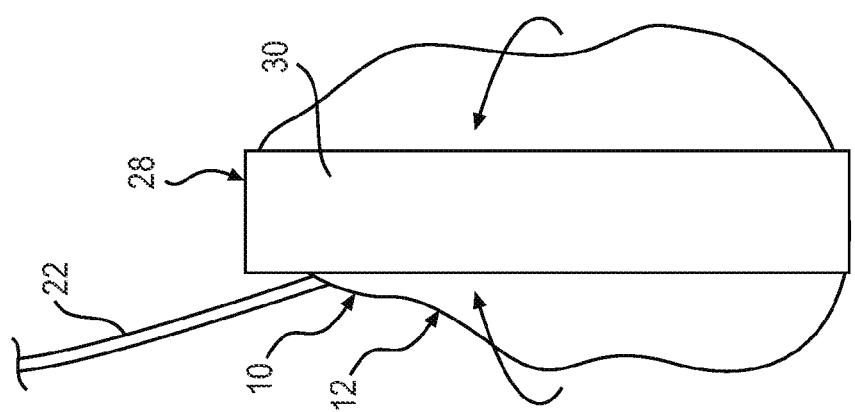

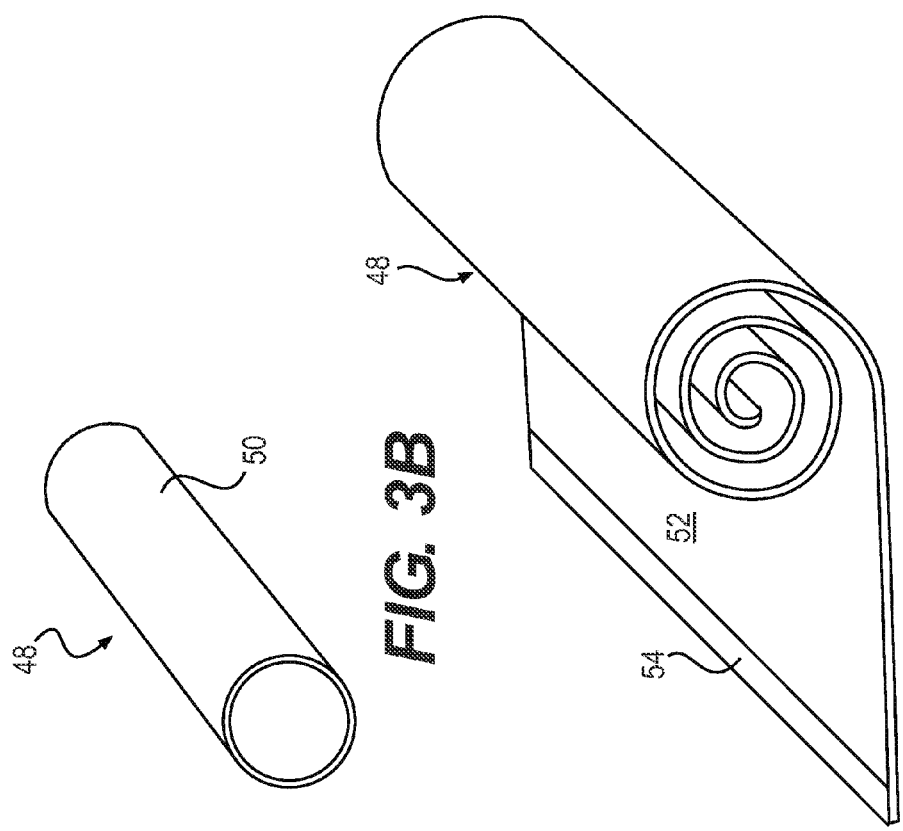
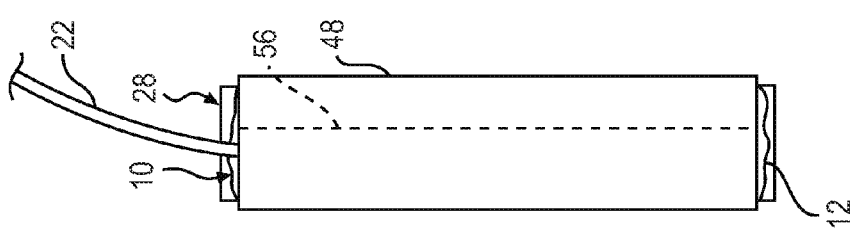

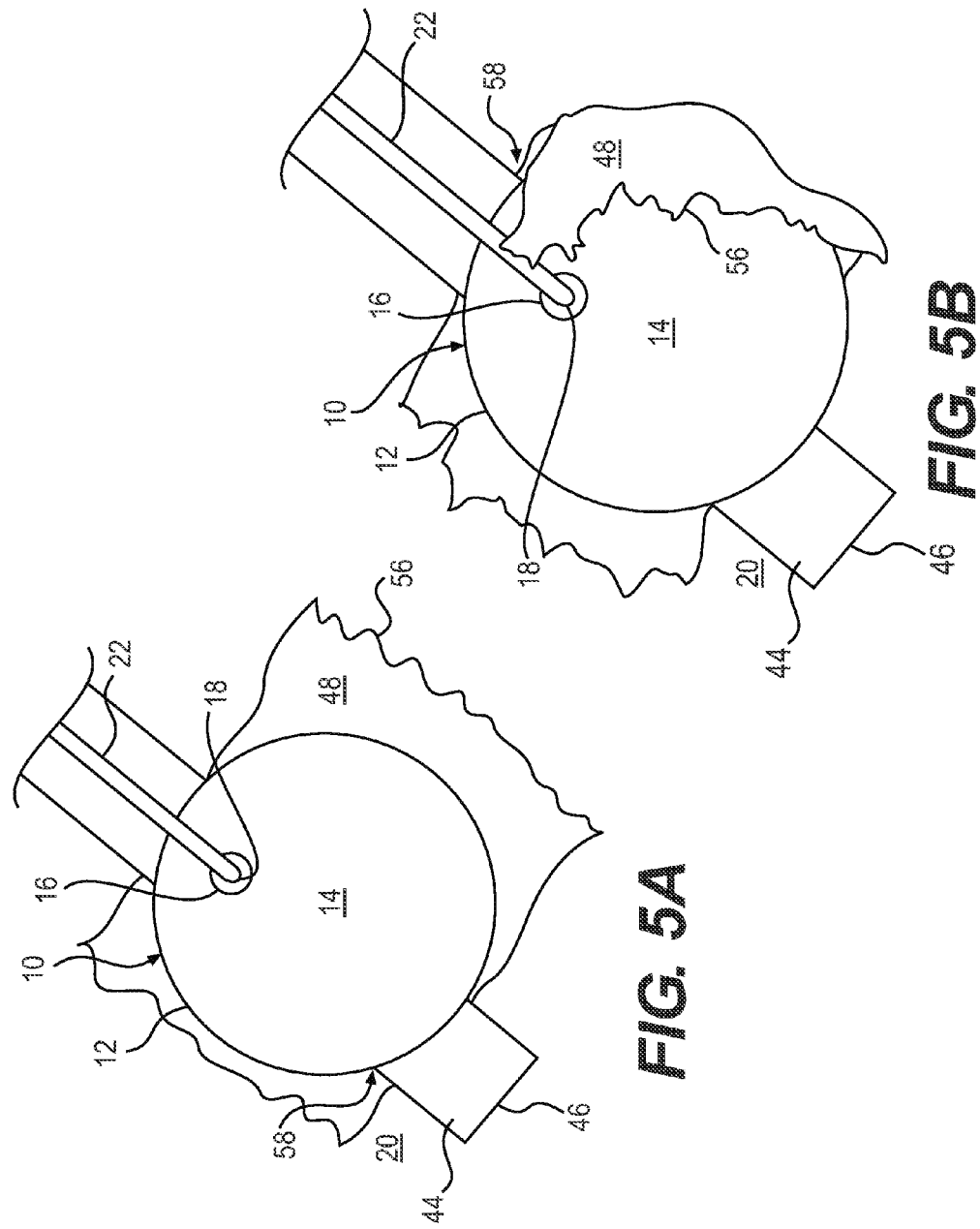

INTRAGASTRIC BALLOON DELIVERY SYSTEMS AND METHODS

CROSS-REFERENCE TO RELATED APPLICATIONS

This application claims the benefit of priority from U.S. Provisional Application No. 61/953,030, filed on Mar. 14, 2014, which is incorporated by reference herein in its entirety.

FIELD OF THE DISCLOSURE

Embodiments of this disclosure relate to intragastric expandable members including, but not limited to, balloons. In particular, embodiments of the present disclosure relate to systems and methods for inserting and deploying intragastric balloons.

BACKGROUND OF THE DISCLOSURE

An intragastric expandable member, such as, e.g., a balloon, may be inserted into a subject's stomach for, among other things, treating obesity. The intragastric balloon may be delivered transorally while deflated with the assistance of an endoscope. Visualization through the endoscope may be important for achieving proper placement of the intragastric balloon. Visualization may be hindered by the intragastric balloon during delivery, depending on the orientation of the intragastric balloon relative to the endoscope. For example, pushing the intragastric balloon ahead of the endoscope may hinder visualization by obstructing the view of an imaging device at a distal end of the endoscope. Moving the intragastric balloon to a side of the endoscope, so that the intragastric balloon and endoscope are side-by-side, may aid visualization. However, it may also make it more difficult to maneuver the intragastric balloon and/or the endoscope due to a narrow diameter of the esophagus relative to a cross-sectional dimension of the intragastric balloon and endoscope when side-by-side.

In view of the above, there remains a need for systems and methods for delivering and deploying intragastric expandable members, such as, e.g., balloons, in a subject's stomach (or in other anatomical portions) in a reliable and efficient manner, and in a manner that aids visualization without hindering maneuverability.

SUMMARY OF THE DISCLOSURE

According to aspects of the present disclosure, a system may include a loading device including an exterior surface. The system may also include an expandable member mounted on the exterior surface of the loading device. The expandable member may be configured to selectively transition between a collapsed state and an expanded state. The system may also include a covering mounted on the expandable member. The covering may extend around the expandable member and the loading device. The loading device may be configured to position the expandable member and the covering for mounting on an exterior surface of an elongate introduction sheath.

Various embodiments of the device may include one or more of the following features: the expandable member may include an intragastric balloon; the loading device may include one of a substantially cylindrical tube defining a lumen therethrough, and a substantially cylindrical rod; the expandable member may extend circumferentially around the loading device; the exterior surface of the loading device may include a lubricious coating; the covering may compress the expandable member against the exterior surface of the loading device; the covering may be one of a tube surrounding at least a portion of the expandable member and a sheet of film wrapped around at least a portion of the expandable member; the covering may be made of a heat-shrink material; the covering may be made of at least one of a digestible material, silicone, polyurethane, plastic, and an elastomer; the loading device may have an outer diameter substantially equal to an outer diameter of the introduction sheath; the loading device may have an inner diameter substantially equal to an outer diameter of the introduction sheath; and/or the introduction sheath may include an endoscope or endoscope sheath.

According to other aspects of the present disclosure, a system may include an endoscope including an exterior surface and a distal end. The system may also include an intragastric balloon mounted on the exterior surface of the endoscope, proximal the distal end of the endoscope. The intragastric balloon may be inflatable from a deflated state to an inflated state. The system may also include a covering mounted on the intragastric balloon. The covering may extend circumferentially around the intragastric balloon and the endoscope, and may be configured to separate from the intragastric balloon when the intragastric balloon is inflated.

Various embodiments of the device may include one or more of the following features: the covering may be one of a tube surrounding at least a portion of the intragastric balloon and a sheet of film wrapped around at least a portion of the intragastric balloon; the covering may be configured to tear along a weakened region formed in the covering; the covering may compress the intragastric balloon against the exterior surface of the endoscope; the covering may include an elastomeric tube; the covering may include a sheet of material wrapped around the intragastric balloon and the endoscope; the covering may be made of heat-shrink material; and/or the covering may be made of digestible material.

According to other aspects of the present disclosure, a method for deploying an expandable member may include inserting an endoscope in a body lumen with the expandable member and a covering around the expandable member mounted around a distal portion of the endoscope. The method may also include positioning the distal portion of the endoscope in a target area. The method may also include expanding the expandable member to release the covering, and deploying the expandable member from the endoscope Various embodiments of the device may include one or more of the features listed below. The step of expanding the expandable member may tear the covering to release the covering. The step of expanding the expandable member may include inflating the expandable member.

Additional characteristics, features, and advantages of the described embodiments will be set forth in part in the description that follows, and in part will be apparent from the description, or, may be learned by practicing the disclosure. The disclosed subject matter can be realized and attained by way of the elements and combinations particularly pointed out in the appended claims.

It is to be understood that both the foregoing general description and the following detailed description are exemplary and explanatory only, and are not restrictive of the described embodiments, as claimed.

BRIEF DESCRIPTION OF THE DRAWINGS

The accompanying drawings, which are incorporated here and constitute a part of this specification, illustrate exemplary embodiments of the present disclosure and, together with the description, serve to explain the principles of the disclosure.

FIG. 1A shows a side view of an intragastric balloon and a loading device, according to aspects of the present disclosure;

FIG. 1B shows a cross-sectional view of a loading device, according to aspects of the present disclosure;

FIG. 1C shows a cross-sectional view of a loading device, according to aspects of the present disclosure;

FIG. 2A shows an intragastric balloon being mounted on a loading device, according to aspects of the present disclosure;

FIG. 2B shows an intragastric balloon mounted on a loading device, according to aspects of the present disclosure;

FIG. 3A shows an intragastric balloon, a loading device, and a covering, according to aspects of the present disclosure;

FIG. 3B shows a perspective view of a covering, according to aspects of the present disclosure;

FIG. 3C shows a perspective view of a covering, according to aspects of the present disclosure;

FIG. 5A shows a side view of an intragastric balloon in a deployed configuration, a torn covering, and an endoscope according to aspects of the present disclosure; and FIG. 5B shows a side view of an intragastric balloon in a deployed configuration, a torn covering, and an endoscope according to aspects of the present disclosure.

DESCRIPTION OF THE EMBODIMENTS

Figure 4:
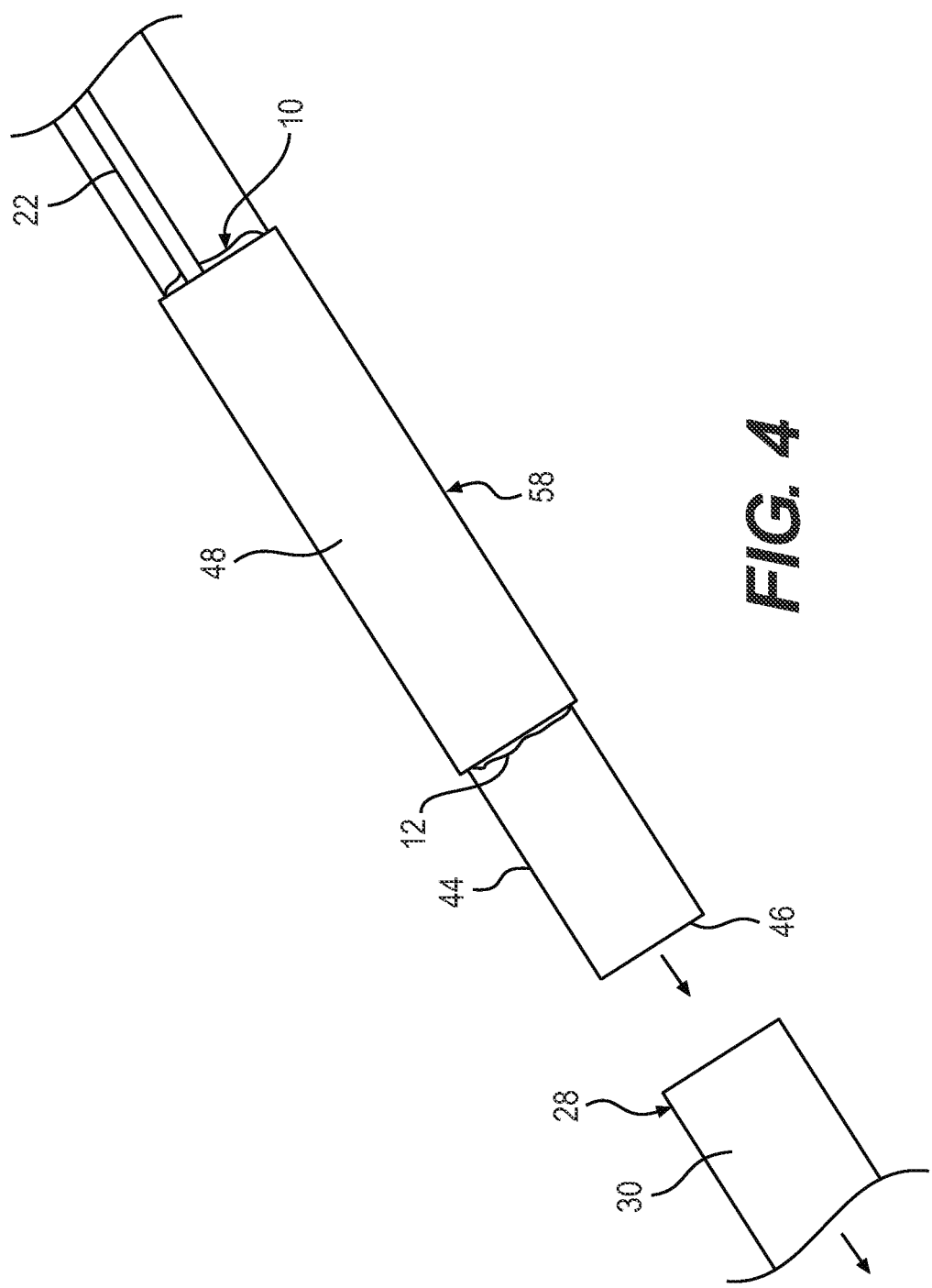
FIG. 4 shows a side view of an intragastric balloon and covering being mounted on an endoscope, after being removed from a loading device, according to aspects of the present disclosure.

Reference will be made in detail to embodiments of the present disclosure, examples of which are illustrated in the accompanying drawings. Wherever possible, the same reference numbers will be used throughout the drawings to refer to the same or like parts. The term "distal" refers to a portion farthest away from a user when introducing a device into a subject. By contrast, the term "proximal" refers to a portion closest to the user when placing the device into the subject.

Overview

Embodiments of the present disclosure relate to systems and methods for mounting an intragastric expandable member, such as, e.g., a balloon, and a covering or other protective member surrounding the intragastric balloon, on a distal portion of an endoscope or other suitable sheath. The intragastric balloon and covering may be mounted on a loading device prior to being mounted on the distal portion of the endoscope. After the intragastric balloon and covering are mounted on the distal portion of the endoscope, the assembly may be positioned within a subject's stomach or another suitable anatomical portion. The intragastric balloon may be expanded, with its expansion causing the covering to tear and separate from the intragastric balloon. The intragastric balloon may remain deployed in the stomach, while the other components may be removed. The covering may be retrieved or digested for removal.

EXEMPLARY EMBODIMENTS

An intragastric expandable member may include, for example, foam, a cage, a stent, or other suitable expandable member, and in one embodiment, the intragastric expandable member may include a balloon 10. It should be understood that the intragastric balloon 10 could be replaced with any other suitable expandable member, including those listed above.

The intragastric balloon 10 is shown in FIG. 1A in an undeployed or deflated configuration. The intragastric balloon 10 may include a membrane 12 surrounding an interior region 14 configured to receive an inflation fluid, such as air, gel saline, or any other suitable fluid. The membrane 12 may be flexible. It is also contemplated that the membrane 12 may be substantially elastic so that it may stretch when subjected to a stretching force, but may return to its unstretched form when the stretching force is removed. The membrane 12 may be made of a polyether block amide like PEBAX, silicone, polyurethane, an elastomer, and/or any other suitable material. It is also contemplated that the membrane 12 may include one or more radiopaque markers (not shown). The radiopaque markers may be, for example, positioned on an outer surface of the membrane 12, embedded within the membrane 12, and/or positioned on an inner surface of the membrane 12. The radiopaque markers may include, for example, printed radiopaque material, a radiopaque band, one or more discrete radiopaque bodies arranged in a predetermined pattern, and/or any other suitable arrangement visible via x-ray imaging.

The intragastric balloon 10 may also include a valve 16. The valve 16 may open to create a passage 18. The passage 18 may provide a path for fluid communication between the interior region 14 and an exterior region 20. The valve 16 may close to seal the passage 18 and prevent fluid communication between the interior and exterior regions 14 and 20. The valve 16 may be self-sealing so that the passage 18 may be closed in the absence of a force keeping the passage 18 open. The valve 16 could be a one-way valve, a gel-seal valve, and/or any other suitable valve.

The valve 16 may receive a tube 22. A distal portion 24 of the tube 22 may extend into the interior region 14 of the intragastric balloon 10. A proximal portion 26 of the tube 22 may be coupled to an inflation fluid source (not shown). The inflation fluid source may be configured to supply air, saline, or any other suitable inflation fluid into the interior region 14, via the tube 22. The supply of inflation fluid may expand the intragastric balloon 10 into its deployed or inflated configuration. The tube 22 may be removed from the intragastric balloon 10 by pulling proximally on the tube 22 to slide the tube 22 out of the interior region 14 and out of the valve 16. Once the tube 22 is pulled out of the valve 16, the passage 18 may close.

A loading device 28 is shown next to the intragastric balloon 10 in FIG. 1A. The loading device 28 may be substantially cylindrical, but may include any suitable shape or configuration. As shown in FIGS. 2A and 2B, the intragastric balloon 10 may be wrapped around or otherwise disposed about the loading device 28. For example, one end of the intragastric balloon 10 may be held manually or by a gripping device against the loading device 28, and then the loading device 28 may be rotated about its longitudinal axis to roll the intragastric balloon 10 around the loading device 28. Additionally or alternatively, the intragastric balloon 10 may be placed around the loading device 28 and twisted. The loading device 28 may be used to help keep the intragastric balloon 10 in a position that makes it easier to mount on an endoscope 44 (FIG. 4).

The loading device 28 is shown in FIG. 1A with a length similar to the length of the intragastric balloon 10. However, it is contemplated that the loading device 28 may be longer than the intragastric balloon 10, so that it may be easier to hold the loading device 28 while wrapping the intragastric balloon 10 around the loading device 28. Alternatively, the loading device 28 may be shorter than the intragastric balloon 10 so that there is less contact, and thus reduced friction, between the loading device 28 and the intragastric balloon 10 once the intragastric balloon 10 is wrapped around the loading device 28.

As shown in FIG. 1B, the loading device 28 may include a tube 30 having a wall 32 with an outer surface 34 and an inner surface 36, and a passage 38. Alternatively, as shown in FIG. 1C, the loading device 28 may include a rod 40 having an outer surface 42. The loading device 28 may be made of a rigid plastic, metal, and/or any other suitable material that may resist being deformed as the intragastric balloon 10 is wrapped around the loading device 38. It is contemplated that the loading device 28 may include one or more openings/cutouts to reduce its weight while reducing material costs. The openings/cutouts may be polygonal, circular, and/or irregularly shaped, and may be arranged in a pattern about the loading device 28.

Alternatively, the loading device 28 may be selectively radially expandable and contractible. For example, the tube 30 may be made of a flexible and/or elastic material, and may be inflated to an at least partially radially expanded state. The intragastric balloon 10 may be wrapped around or otherwise disposed about the radially expanded tube 30. The tube 30 may be removed from the intragastric balloon 10 by deflating to an at least partially radially contracted state and sliding the tube 30 out of or otherwise away from the intragastric balloon 10. Alternatively, the loading device 28 may be mechanically expanded, and could include an expandable/contractible stent, cage, basket, or similar device.

It is also contemplated that one or more surfaces of the loading device 28 may be coated with a lubricious material, such as a polytetrafluoroethylene (PTFE) like TEFLON, polyvinylchloride, high-density polyethylene (HDPE), or the like, that may reduce friction between the loading device 28 and the intragastric balloon 10 applied thereon. Alternatively, it is also contemplated that the outer surface 34 and/or outer surface 42 may include an adhesive coating that has adhesive properties when applied, but loses its adhesive properties when it undergoes a temperature change or is exposed to another substance. The coating may help hold the intragastric balloon 10 on the loading device 28 initially, without hindering release of the intragastric balloon 10 from the loading device 28 later when its temperature changes or it is exposed to another substance. The temperature change may, for example, be caused by direct or indirect contact with a user's hand.

A covering 48, shown in FIG. 3A, may be applied around the intragastric balloon 10 and the loading device 28. The covering 48 may hold the intragastric balloon 10 on the loading device 28. For example, the covering 48 may compress the intragastric balloon 10 against the loading device 28. It is also contemplated that the covering 48 may hold the tube 22 on the loading device 28 by, for example, compressing the tube 22 against the loading device 28. The covering 48 may include a tube 50 (FIG. 3B), a sheet of material 52 (FIG. 3C), and/or any other suitable covering.

The tube 50 may be positioned around the intragastric balloon 10 after the intragastric balloon 10 has been wrapped around the loading device 28. The tube 50 may be made of or include plastic, silicone, polyurethane, an elastomer, a digestible material such as collagen or glucose, and/or any other suitable digestible or non-digestible material. The tube 50 may have elastomeric properties, such that the tube 50 may be expanded when positioned over the intragastric balloon 10 and loading device 28, and then allowed to contract to compress the intragastric balloon 10 against the loading device 28. Additionally or alternatively, the tube 50 may be heat-shrinkable so heat from a heat source may cause the tube 50 to contract and compress the intragastric balloon 10 against the loading device 28. For example, the tube 50 may be made of a mechanically expanded extruded nylon or polyolefin tube, which may shrink when heated. The shrinking may take place in one plane, along the diameter of the tube 40, to reduce the diameter to a fraction of the original diameter.

Alternatively, the sheet 52 may be wrapped around the intragastric balloon 10 after the intragastric balloon 10 has been wrapped around the loading device 28. The sheet 52 may be made of a thin film, and may cling to itself, the intragastric balloon 10, and/or the loading device 28 when wrapped. While not required, it is contemplated that an adhesive 54 may be applied to one or more edges or surfaces of the sheet 52 to help the sheet 52 adhere to itself, the intragastric balloon 10, and/or the loading device 28. The sheet 52 may be made of or include plastic, silicone, polyurethane, an elastomer, a digestible material like collagen, glucose, and/or any other suitable digestible or non-digestible material.

At least one layer of the sheet 52 may surround the intragastric balloon 10 and loading device 28. It is also contemplated that a plurality of layers of the sheet 52 may surround the intragastric balloon 10 and loading device 28. Tension may be applied to the sheet 52 during wrapping so that the sheet 52 may compress the intragastric balloon 10 against the loading device 28. Additionally or alternatively, the sheet 52 may be heat-shrinkable so heat from a heat source may cause one or more layers of the sheet 52 to contract and compress the intragastric balloon 10 against the loading device 28. For example, the sheet 52 may be made of a nylon or polyolefin film, which may shrink when heated. The shrinking may take place in a transverse plane, along the width of the sheet 52, to reduce the width to a fraction of the original width.

The covering 48 may include one or more weakened regions 56. The weakened region 56 may include, for example, a portion of the covering 48 with a preformed cut or tear, a perforated portion, a portion that may be thinner than other portions, a portion that reacts to bodily fluids and/or heat by weakening (e.g., at least partially dissolving), and/or any other suitable weakened region. When the covering 48 is stressed by inflation of the intragastric balloon 10, the covering 48 may tear along the weakened region 56. The weakened region 56 may be applied to the covering 48 after the covering 48 has been mounted around the intragastric balloon 10 and the loading device 28, or alternatively, prior to being mounted. It is also contemplated that at least a portion of the covering 48 may be coupled to the tube 22 by being wrapped around a portion of the tube 22, and/or adhered to the tube 22 by any suitable adhesive.

The covering 48 may have a longitudinal length similar to the longitudinal length of the intragastric balloon 10. Alternatively, the covering 48 may have a longitudinal length greater than that of the intragastric balloon 10, to ensure the covering 48 compresses ends of the intragastric balloon 10 inward toward the loading device 28. Alternatively, the covering 48 may have a longitudinal length less than that of the intragastric balloon 10, to ensure that inflating the intragastric balloon 10 will cause a tear to propagate across all or almost all of the longitudinal length of the covering 48.

Alternatively, the covering 48 may include at least one discrete ring or band (not shown). For example, the covering 48 may include a combination of discrete bands including a band around a proximal portion of the intragastric balloon 10, another band around an intermediate portion of the intragastric balloon 10, and/or a band around a distal portion of the intragastric balloon 10, for securing the intragastric balloon 10 about the loading device 28.

After the intragastric balloon 10 and the covering 48 are mounted around the loading device 28, the components may be packaged. The packaged components may be shipped to users, such as, e.g., healthcare providers. The covering 48 may help keep the intragastric balloon 10 mounted on the loading device 28 during shipping, by compressing the intragastric balloon 10 against the loading device 28.

The user may already have an elongate sheath, such as an endoscope, catheter, or other suitable introduction sheath 44 (FIG. 4), and may mount the intragastric balloon 10 and the cover 48 on the outer surface of the endoscope 44, for insertion into a subject's body. The loading device 28 may be removed prior to insertion. For example, the loading device 28 may position the intragastric balloon 10 and the covering 48 so that they may be quickly mounted on the endoscope 44. The loading device 28 may be disposed of afterwards.

The outer diameter of the loading device 28, which may include the tube 30 or the rod 40, may be substantially equal to or slightly larger than the outer diameter of the endoscope 44. The loading device 28 may be removed from within the intragastric balloon 10 surrounding the loading device 28, and the endoscope 44 may be positioned in the space previously occupied by the loading device 28. Removing the loading device 28 may include pushing, pulling, contracting (e.g., by deflating or otherwise drawing side portions radially inward), and/or twisting the loading device 28 to separate it from the intragastric balloon 10 and/or the covering 48. Removing the loading device 28 may also include cutting or tearing the loading device 28, allowing it to be at least partially contracted or collapsed, so that it may be removed.

Additionally or alternatively, an end face 46 of the endoscope 44 may be moved into engagement with an end of the loading device 28, and due to their diameters, the end face 46 may push the loading device 28 out from within the wrapped intragastric balloon 10, leaving the intragastric balloon 10 wrapped around the endoscope 44 while being covered by the covering 48. This allows the endoscope 44 to support the intragastric balloon 10 and covering 48 as the loading device 28 is removed, thus ensuring that portions of the intragastric balloon 10 will not move radially inward and obstruct insertion of the endoscope 44.

Alternatively, the inner diameter of the tube 32 may be substantially equal to the outer diameter of the endoscope 44, allowing the endoscope 44 to slide into the passage 38 of loading device 28. With this arrangement, the tube 32, intragastric balloon 10, and covering 48 may be mounted around the endoscope 44. An exposed portion of the tube 32 may be pulled, pushed, and/or twisted to move the tube 32 off of the endoscope 44, while leaving the intragastric balloon 10 and covering 48 around the endoscope 44. The thickness of the wall 30 of the tube 32 may be sufficiently large so the tube 32 may not buckle when wrapped with the intragastric balloon 10, yet thin enough so that a gap between the inner surface 36 of the tube 32 and the outer surface of the endoscope 44 may be minimized once the tube 32 has been removed from the endoscope 44. Loading devices with various dimensions may be used to accommodate endoscopes of various dimensions.

Although not required, it is contemplated that the diameter of the covering 48 may tend to shrink after the intragastric balloon 10 and the covering 48 have been mounted on the endoscope 44. For example, the covering 48 may contract, due to its elasticity, when the loading device 28 is removed, thus compressing the intragastric balloon 10 against the outer surface of the endoscope 44. Additionally or alternatively, the covering 48 may be heat-shrinkable so heat from a heat source may cause the covering 48 to contract and compress the intragastric balloon 10 against the endoscope 44. Shrinkage of the covering 48 after mounting on the endoscope 44 may be desirable because it may provide for the ability to accommodate endoscopes having a variety of diameters. The covering 48 and intragastric balloon 10 may be made large enough to be positioned over a variety of endoscopes, and when one of those endoscopes is inserted and loading device 28 is removed, the covering 48 may be shrunk to compress the intragastric balloon 10 against the endoscope regardless of the endoscope's diameter. Alternatively, it is contemplated that the loading device 28 may be omitted, and the intragastric balloon 10 and covering 48 may be mounted directly onto the outer surface of the endoscope 44.

FIG. 4 shows the intragastric balloon 10 wrapped around a distal portion 48 of the endoscope 44, and the covering 48 holding the intragastric balloon 10 around the distal portion 58 and/or compressing the intragastric balloon 10 against the distal portion 58. The distal portion 48 may be inserted into a subject's mouth, and maneuvered into the stomach through the esophagus. In alternative embodiments, the distal portion 48 may be inserted through any other natural cavity/orifice or surgical incision. Because the intragastric balloon 10 and covering 48 are mounted around a side portion of the endoscope 44, visualization through the distal end of the endoscope may remain unobstructed by the intragastric balloon 10 and covering 48. Furthermore, because the covering 48 holds and/or compresses the intragastric balloon 10 and the tube 22 against the endoscope 44, the overall diameter of the assembly is kept small, making it easier to navigate the assembly to the stomach through the esophagus.

Once the intragastric balloon 10 and covering 48 are in the stomach, the inflation fluid may be directed into the intragastric balloon 10 through the tube 22, causing the intragastric balloon 10 to expand to its deployment configuration. During expansion of the intragastric balloon 10, the diameter of the intragastric balloon 10 may increase to a point where the intragastric balloon 10 may tear the covering 48 (FIGS. 5A and 5B). The covering 48 may begin tearing at the weakened region 56, and the tear may then propagate across a length of the covering 48. It is also contemplated that if the covering 48 is made of a digestible material, the digestive fluids in the stomach may help weaken the covering 48 to aid tearing. It is also contemplated that if the covering 48 is made of or includes a material that reacts to body heat or chemistry by weakening, its introduction into the body may help weaken the covering 48 to aid tearing.

The tear may extend along an entire length of the covering 48, or along at least a portion of the length of the covering 48. The torn covering 48 may separate from the intragastric balloon 10. The user may pull the tube 22 proximally out of the intragastric balloon 10 and valve 16, and withdraw the tube 22 and endoscope 44 from the stomach, leaving the inflated intragastric balloon 10 deployed in the stomach. The inflated intragastric balloon 10 may remain in the stomach for a prescribed period of time. It is contemplated that the inflated intragastric balloon 10 may be anchored in the stomach by one or more anchoring devices (not shown), including, for example, one or more clips, sutures, and/or similar anchors.

The torn covering 48 may be removed from the subject's stomach. For example, the torn covering 48 may be retrieved using a grasping device, such as a hook, clamp, or forceps, and pulled proximally for removal through the subject's esophagus. Additionally or alternatively, if the covering 48 is made of a digestible material, the torn covering 48 may be removed by being digested in the patient's stomach. Additionally or alternatively, at least a portion of covering 48 may be attached to the tube 22 (FIG. 5B), and may be pulled out of the stomach together with the tube 22.

Although the embodiments described above are disclosed in the context of an endoscope, those skilled in the art will understand that the principles disclosed above can be applied to other types of devices and can be implemented in different ways without departing from the scope of the invention as defined by the claims. In particular, constructional details, including manufacturing techniques and materials, are well within the understanding of those of ordinary skill in the art and have not been disclosed in detail herein. These and other modifications and variations are well within the scope of the present disclosure and can be envisioned and implemented by those of ordinary skill in the art.

Moreover, while specific embodiments may have been illustrated and described collectively herein, it should be appreciated that any subsequent arrangement designed to achieve the same or similar purpose may be substituted for the specific embodiments described and shown herein. This disclosure is intended to cover any and all subsequent adaptations or variations of the various embodiments. Combinations of the above embodiments, and other embodiments not specifically described herein, will be apparent to those of ordinary skill in the art upon reviewing the present disclosure. Further, one or more features described in one of the above-described embodiments, may be used with one or more features described in any of the other above-described embodiments.

Other embodiments of the present disclosure will be apparent to those skilled in the art from consideration of the specification and practice of the embodiments disclosed herein. It is intended that the specification and examples be considered as exemplary only, and departure in form and detail may be made without departing from the scope and spirit of the present disclosure as defined by the following claims.

What is claimed is:

1. A system, comprising:
a loading device including an exterior surface, wherein the loading device is radially contractible from an expanded state to a contracted state, and wherein the loading device includes at least one of a contractible stent, cage, or basket;
an expandable member mounted on the exterior surface of the loading device, the expandable member being configured to selectively transition between a collapsed state and an expanded state, wherein the expandable member includes an intragastric balloon; and
a covering mounted on the expandable member, the covering extending around the expandable member and the loading device, and the loading device being configured to position the expandable member and the covering for mounting on an exterior surface of an introduction sheath.

2. The system of claim 1, wherein the loading device includes one of a substantially cylindrical tube defining a lumen therethrough, and a substantially cylindrical rod.

3. The system of claim 1, wherein the expandable member extends circumferentially around the loading device.

4. The system of claim 1, wherein the loading device is configured to be deflated to radially contract from the expanded state to the contracted state.

5. The system of claim 1, wherein the covering compresses the expandable member against the exterior surface of the loading device.

6. The system of claim 1, wherein the covering is one of a tube surrounding at least a portion of the expandable member and a sheet of film wrapped around at least a portion of the expandable member.

7. The system of claim 1, wherein the covering is made of at least one of a heat-shrink material, a digestible material, silicone, polyurethane, plastic, and an elastomer.

8. The system of claim 1, wherein the loading device has an outer diameter substantially equal to an outer diameter of the introduction sheath.

9. The system of claim 1, wherein the loading device has an inner diameter substantially equal to an outer diameter of the introduction sheath.

10. A system, comprising:
a loading device including an exterior surface, wherein the loading device is radially contractible from an expanded state to a contracted state, and wherein the loading device includes at least one of a contractible stent, cage, or basket;
an expandable member mounted on the exterior surface of the loading device, the expandable member being configured to selectively transition between a collapsed state and an expanded state, wherein the expandable member includes an intragastric balloon; and
a covering made from a digestible material and mounted on the expandable member, the covering extending around the expandable member and the loading device.

11. The system of claim 10, wherein the loading device includes one of a substantially cylindrical tube defining a lumen therethrough, and a substantially cylindrical rod.

12. The system of claim 10, wherein the expandable member extends circumferentially around the loading device.

13. The system of claim 10, wherein the covering compresses the expandable member against the exterior surface of the loading device.

14. The system of claim 10, wherein the loading device is configured to position the expandable member and the covering for mounting on an exterior surface of an introduction sheath.

15. A method for deploying an expandable member, comprising:
positioning a loading device, an expandable member, and a covering over an exterior surface of a distal portion of an endoscope,
wherein the loading device includes an exterior surface, wherein the loading device is radially contractible from an expanded state to a contracted state, and wherein the loading device includes at least one of a contractible stent, cage, or basket,
wherein the expandable member is mounted on the exterior surface of the loading device, the expandable member being configured to selectively transition between a collapsed state and an expanded state, wherein the expandable member includes an intragastric balloon, and wherein the covering is mounted on the expandable member, the covering extending around the expandable member and the loading device, and the loading device being configured to position the expandable member and the covering for mounting on an exterior surface of an endoscope;

transitioning the loading device from the first state to the second state; removing the loading device from the exterior surface of the endoscope; inserting an endoscope in a body lumen with the expandable member and the covering around the expandable member mounted around the distal portion of the endoscope;

positioning the distal portion of the endoscope in a target area; expanding the expandable member to release the covering; and deploying the expandable member from the endoscope.

16. The method of claim 15, wherein expanding the expandable member tears the covering to release the covering.

17. The method of claim 15, wherein expanding the expandable member includes inflating the expandable member.

* * * * *